US008658813B2

(12) United States Patent
Korlipara et al.

(10) Patent No.: US 8,658,813 B2
(45) Date of Patent: Feb. 25, 2014

(54) POLYOL ESTERS OF MEDIUM CHAIN FATTY ACIDS AND PROCESS FOR PREPARATION THEREOF

(75) Inventors: Venkata Padmaja Korlipara, Hyderabad (IN); Venkata Surya Koppeswara Rao Bhamidipati, Hyderabad (IN); Satya Bhaskar Potula, Hyderabad (IN); Badari Narayana Prasad Rachapudi, Hyderabad (IN); Arun Kumar Singh, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 221 days.

(21) Appl. No.: 12/992,344

(22) PCT Filed: May 14, 2009

(86) PCT No.: PCT/IN2009/000286

§ 371 (c)(1), (2), (4) Date: Jun. 6, 2011

(87) PCT Pub. No.: WO2009/139005

PCT Pub. Date: Nov. 19, 2009

(65) Prior Publication Data

US 2011/0263885 A1 Oct. 27, 2011

(30) Foreign Application Priority Data

May 14, 2008 (IN) ........................... 1201/DEL/2008

(51) Int. Cl.
*C11C 3/00* (2006.01)
*A01H 5/00* (2006.01)
*A23D 9/00* (2006.01)

(52) U.S. Cl.
USPC ........................... 554/168; 554/223; 554/227

(58) Field of Classification Search
USPC ......................................... 554/168, 223, 227
See application file for complete search history.

(56) References Cited

U.S. PATENT DOCUMENTS

| | | | | |
|---|---|---|---|---|
| 3,148,147 A * | 9/1964 | Bell et al. | ...................... | 508/251 |
| 4,992,292 A * | 2/1991 | Klemann et al. | .............. | 426/611 |
| 5,663,042 A * | 9/1997 | Grieve et al. | .................. | 430/619 |

FOREIGN PATENT DOCUMENTS

| | | | |
|---|---|---|---|
| EP | 1533360 A1 * | 5/2005 | ........... C10M 105/38 |
| JP | 11-236584 A | 8/1999 | |
| JP | 2006-313191 A | 11/2006 | |
| WO | 91/15455 A1 | 10/1991 | |

OTHER PUBLICATIONS

Tanaka, Masahide et al: "Refrigerant compositions containing carbon dioxide and lubricating oils" XP002546123 retrieved from STN Database accession No. 1999:556902, 1999.*

Maties, Marius I. et al : "Study of the lubricating properties of pentaerythritol esters of saturated linear monocarboxylic acids" XP002546124'retrieved from STN Database accession No. 1986:6533, 1986.*

D. Ravi and Hari Babu Mereyala: "A new mild method for the synthesis of esters and benzenethiol esters by activation of pyridine-2-thiol or benzothiazol-2-thiol esters by methyl iodide" Tetrahedron Letters., vol. 30, No. 44, 1989, pp. 6089-6090.*

Nanu, Ion et al: "Plasticizer properties of neoalkyl diesters" XP002546126 retrieved from STN Database 'accession No. 1979:508595, 1979.*

Isobe, Kazuya et al: ft Electrophotographic toner containing higher ester-releasing agent XP00254612.5 retlieved from STN Database accession No. 2006:1201503, 2006.*

Junichi Yoshida, Masanoriitoh, Shinichiro Matsunaga, • Sachihiko Isoe: "Electrochemical oxidation of acylsilanes and their tosylhydrazones" Journal of Organic Chemistry., vol. 57, No. 18, Aug. 1992, pp. 4877-4882.*

International Search Report mailed Sep. 30, 2009; PCT/IN2009/000286.

* cited by examiner

*Primary Examiner* — Deborah D Carr
(74) *Attorney, Agent, or Firm* — Ladas & Parry LLP

(57) ABSTRACT

A new class of oleochemical based polyol esters of general formula 1 are prepared by esterification of different polyols having 5-6 carbon atoms and 2-4 hydroxyl groups with 10-undecenoic acid or/and undecanoic acid with a hydroxyl value of ≤1.0 mg KOH/g. Wherein $R_1$, $R_2$, $R_3$ is selected from a group consisting of $CH_3$—, $CH_3CH_2$—, —$CH_2OCOR_4$ wherein $R_4$ is selected from $CH_2{=}CH{-}(CH_2)_8$— or $CH_3{-}(CH_2)_9$—, individually or in combination thereof. The resulting esters were characterized for lubricant properties like viscosity, viscosity index, pour point, flash point and copper corrosion tests. The properties indicate their potential as promising lubricant base stocks for automotive lubricants, metal working oil, hydraulic oil and other industrial applications. Vegetable oils provide most of the desirable lubricant properties such as good boundary lubrication, high viscosity index, high flash point and low volatility. Synthetic esters prepared from renewable resources like vegetable oils exhibit better performance at a lower cost compared to mineral oil based synthetic esters.

$$R_2{-}\underset{R_3}{\overset{R_1}{\underset{|}{\overset{|}{C}}}}{-}CH_2{\cdot}O{\cdot}CO{\cdot}R_4 \quad (I)$$

8 Claims, No Drawings

POLYOL ESTERS OF MEDIUM CHAIN FATTY ACIDS AND PROCESS FOR PREPARATION THEREOF

FIELD OF INVENTION

The present invention relates to the preparation of different polyol esters based on 10-undecenoic acid and undecanoic acid and their evaluation for their properties as potential lubricant base stocks.

BACKGROUND OF THE INVENTION

In recent years the awareness and concern over the use of petroleum based fuels and lubricants and their impact on the environment has opened the quest for environment friendly lubricants from renewable resources like vegetable oils.

Mineral oil based lubricants, generally suffer from many disadvantages such as high toxicity to the environment and poor biodegradability. There is a need for the environment to be protected from the pollution from lubricants which are not environmentally friendly. Also the dependency on the dwindling supply of petroleum feed stock for the production of mineral oil base stocks is also a cause of worry. For these reasons a new class of environmentally acceptable lubricants is available and vegetable oils find a major place among them along with synthetic esters (polyol esters with short chain fatty acids and diesters) which are considerably expensive and can not be used always. The use of vegetable oils as lubricants is known for a long time. In recent years, increasing attention has been paid to natural triglycerides, fatty acids derived from them, and their potential applications. This raw material is cheap and renewable. Moreover, natural fats and products derived from them are generally environmentally friendly. Their lubricity (antiwear, antifriction and load carrying capacity) characteristics are vastly superior to that of mineral oils and these oils can work at much lower viscosities and remove heat faster than hydrocarbon based lubricants. These lubricants are energy efficient and can cause substantial fuel economy in internal combustion engines (Journal of Synthetic Lubrication, Vol. 23, p. 91, 2006). The operating temperature range of vegetable oils and fatty esters depend upon the degree of saturated chain length and type of alcohol moiety. However, glycerol, a component of the triglyceride molecule is readily destructible at high temperatures. This disadvantageous property stems from the presence of hydrogen atoms in β position relative to the hydroxyl group in the glycerol molecule. This structural feature is conductive to the partial fragmentation of the molecule and the formation of unsaturated compounds. The compounds formed undergo polymerization, increasing the liquid's viscosity and resulting in the formation of precipitate particles. This problem can be solved by replacing glycerol with another polyhydric alcohol which does not contain β-hydrogen atoms, like neopentylglycol (NPG), trimethylolpropane (TMP) or pentaerythritol (Industrial Lubrication and Tribology, Vol. 50, p. 6, 1998). Although such alcohols also decompose at high temperatures, their thermal decomposition has a radical character and proceeds slowly. Synthetic esters produced from vegetable oil based fatty acids can not be used at extremely high temperatures, but they are very suitable in less extreme applications such as two-stroke engine oils, chain bar oils, cutting oils, concrete mould release agents and cosmetic ingredients (Bioresource Technology, Vol. 87, p. 35, 2003).

The properties of esters also depend on the structure of the constituent fatty acids and alcohols, i.e., on the length of their aliphatic chain and the number and relative position of unsaturated bonds. Saturated acids are highly resistant to oxidation and high temperature, but their pour point is high due to the linear structure of the acids. Polyunsaturated fatty acids, especially those containing conjugated bonds, are the most susceptible to oxidation and thermal degradation, even though their esters exhibit lower pour points. The best option is to use mono unsaturated fatty acids like oleic acid or other mono unsaturated fatty acids for the manufacture of synthetic oils. Utilisation of non-edible oil fatty acids for the development of lubricant base stocks is recommended due to the shortage of edible oils. One of the most potential non-edible oil is castor oil.

Review article on plant-oil-based lubricants published in Journal of the Science of Food and Agriculture, Vol. 86, p. 1769, 2006 highlights the advantages and disadvantages of plant based lubricants and various chemical modifications like modification of the ester moiety and multiple bonds to improve the undesirable properties of native plant oils.

High performance ester lubricants from natural oils have been reported in Industrial Lubrication and Tribology, Vol. 54, p. 165, 2002. A new class of bio-based esters derived from vegetable oils that exhibit excellent low temperature properties and oxidation stability are discussed. This is possible due to recent advances in the biotechnology of vegetable oils through advanced plant breeding and genetic engineering and the chemical modifications like changing the chain lengths or introducing branching in the acyl/alkyl chains, changing the polyol backbone structure and mixing asymmetry of the backbone/acyl/alkyl chains to convert these natural esters into high performance biolubricants.

Palmolein blends with Palm oil derived polyol esters comprising palm oil by-products having short chain fatty acids ($C_6$ to $C_{12}$) with hindered polyols like neopentylglycol, trimethylolpropane and pentaerythritol as biodegradable functional fluids are described in patent (EP 1533360). The limitation is that these fluids are only suitable for tropical climates with temperature ranging from 15-40° C.

R Yunus et al., reported synthesis and characterisation of TMP esters for chemical and lubricant characteristics from palm kernel oil methyl esters (Journal of Oil Palm Research Vol. 15, p. 42, 2003). The lubrication properties of the TMP esters were compared with commercial vegetable oil based TMP esters. The low temperature properties of the esters prepared were inferior to palm oil TMP esters although their lubrication properties were comparable.

Gryglewicz et al. (Bioresource Technology, Vol 87, p. 35, 2003) described the preparation of polyol esters based on vegetable and animal fats, wherein rapeseed oil, olive oil and lard fatty acid methyl esters were transesterified with NPG and TMP using calcium methoxide as catalyst. Esters of lard fatty acids showed higher pour points because of their high saturated acid content.

TMP esters of rapeseed oil fatty acids were synthesized and evaluated as biodegradable hydraulic fluids in comparison to commercially available hydraulic fluids (Journal of the American Oil Chemists' Society, Vol. 75., 1998). These products exhibited good cold stability, friction and wear characteristics and resistance against oxidation at elevated temperatures.

Trimethyolpropane esters useful as lubricant base for motor-car engine were prepared by total esterification of trimethyolpropane with a mixture of saturated aliphatic acids, dicarboxylic acids and iso-acids (U.S. Pat. No. 4,061,581, 1977)

European patent (EP 0712834; 1996) describes the preparation of polyol esters derived from polyols and aliphatic mono carboxylic acid mixtures derived from natural vegetable oils like rapeseed, sunflower, peanut and soybean, wherein the acid mixtures comprise at least about 72% by weight of oleic acid for possible applications like functional fluids and greases.

Flame retardant hydraulic oils containing partial esters of polyols and acyclic mono carboxylic acids having a total of 6-21 carbons have been reported (U.S. Pat. No. 6,402,983, 2002). Even though both undecanoic and 10-undecenoic acids are used for making polyol esters, these esters were reported to be partial polyol esters with hydroxyl value of ≥35.0 mg KOH/g. This clearly indicates that the partial polyol esters prepared essentially contains considerable amount of hydroxyl moiety.

In the prior art for producing lubricants the vegetable oil fatty acids used are either higher fatty acids like oleic, stearic, palmitic or saturated short chain fatty acids like palm kernel and coconut oil fatty acids. The properties of esters depend on the structure of the constituent fatty acids and alcohols. i.e. on the length of the aliphatic chain and the number and relative position of unsaturated bonds. There were no reports on the preparation of total polyol esters based on 10-undecenoic acid and undecanoic acids containing less than 1.0 mg KOH/g hydroxylic value useful for lubricant application.

OBJECTS OF THE INVENTION

The main objective of the present invention is to provide different polyol esters of 10-undecenoic acid and undecanoic acid.

A further objective of the present invention is to synthesize different polyol esters with a mixture of 10-undecenoic acid and undecanoic acid.

Yet another objective of the present invention is to synthesize different polyol esters with different polyols having 5-6 carbon atoms and a total of 2-4 hydroxyl groups.

Yet further objective of the invention is to make total esters of polyols having a hydroxyl value of ≤1.0 mg KOH/g.

It is also an objective of the present invention is to evaluate the polyol esters for their potential as lubricant base stocks by characterisation for properties like viscosity, viscosity index, pour point, flash point and copper corrosion tests.

SUMMARY OF THE INVENTION

In the present invention novel polyolesters were prepared with pure unsaturated fatty acids undecenoic acid or with its hydrogenated derivative undecanoic acid. Undecenoic acid is generally prepared from castor oil (non edible vegetable oil) using pyrolysis reaction. Different types of lubricant base stocks were prepared with 10-undecenoic acid and undecanoic acid or their mixtures with different polyols have 5-6 carbon atoms and a total of 2-4 hydroxyl groups. The products were characterized for their physico-chemical properties and evaluated for their use as potential lubricant base stocks.

DETAILED DESCRIPTION OF THE INVENTION

Accordingly, the present invention provides a compound of general formula 1

General formula 1

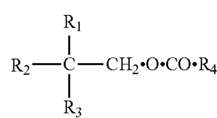

Wherein $R_1$, $R_2$, $R_3$ is selected from a group consisting of $CH_3$, $CH_3CH_2$—, —$CH_2OCOR_4$ wherein $R_4$ is selected from $CH_2$═CH—$(CH_2)_8$— or $CH_3$—$(CH_2)_9$— individually or in combination thereof.

In an embodiment of the present invention wherein $R_1$ and $R_3$ is —$CH_2OCOR_4$; $R_2$ is selected from a group consisting of $CH_3$, $CH_3CH_2$—, —$CH_2OCOR_4$ wherein $R_4$ is selected form $CH_2$═CH—$(CH_2)_8$— or $CH_3$—$(CH_2)_9$— individually or in combination thereof.

In another embodiment of the present invention wherein $R_1$ and $R_3$ is $CH_3$, $R_2$ is —$CH_2OCOR_4$ wherein $R_4$ is selected form $CH_2$═CH—$(CH_2)_8$— or $CH_3$—$(CH_2)_9$— individually or in combination thereof.

In still another embodiment of the present invention wherein the structural formula of the compound of general formula 1 comprising;

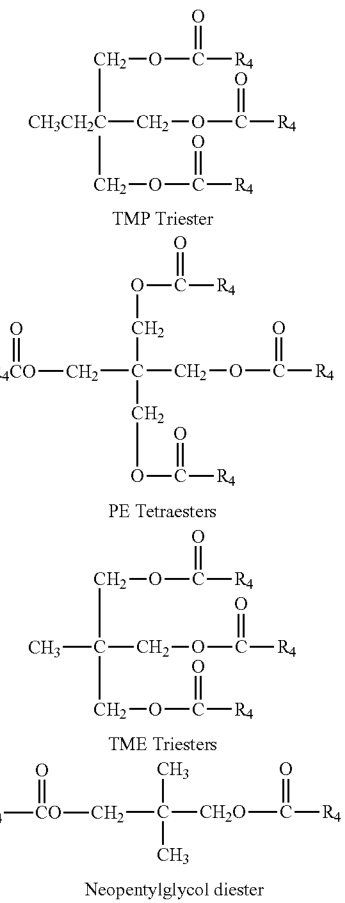

Where R is $CH_2$═CH—$(CH_2)_8$— or $CH_3$—$(CH_2)_9$— or a combination thereof.

In yet another embodiment of the present invention wherein the representative compounds of general formula comprising:

i. Trimethylolpropane Triesters of 10-Undecenoic Acid i.e 2,2-Di[(10-undecenoyloxy)methyl]butyl 10-undecenoate ii. Pentaerythritol Tetra Esters of 10-Undecenoic Acid i.e. 3-(10-Undecenoyloxy)-2,2-di[(10-undecenoyloxy)methyl] propyl 10-undecenoate iii. Trimethylolethane Triesters of 10-Undecenoic Acid i.e. 2-Methyl-3-(10-undecenoyloxy)-2-[(10-undecenoyloxy) methyl]propyl 10-undecenoate iv. Neopentylglycol Diesters of 10-Undecenoic Acid i.e. 2,2-Dimethyl-3-(10-undecenoyloxy)propyl 10-undecenoate v. Trimethylolpropane Triesters of Undecanoic Acid i.e. 2,2-Di[(undecanoyloxy)methyl]butyl undecanoate Accordingly, the present invention provides a process for preparation of compounds of general formula 1 comprising the steps: reacting a medium chain fatty acid such as 10-undecenoic acid, undecanoic acid and their mixtures, with terminal alkenyl group or its hydrogenated form or their mixtures with di, tri and tetrahydric polyols in presence of a catalyst under inert atmosphere at a temperature ranging between 180 to 190° C. for a period ranging between 5 to 7 hr, purifying the compound by distilling out unreacted acid at reduced pressure and treatment with basic alumina.

In an embodiment of the present invention wherein the di, tri and tetrahydric polyols used is selected form a group consisting of neopentylglycol, trimethylolpropane, trimethylolethane and pentaerythritol.

In another embodiment of the present invention wherein the reaction may be carried out using a molar ratio of polyol to carboxylic acid or their mixtures in the range of 1:6 to 1:10

In still another embodiment of the present invention wherein the stannous chloride is used as catalyst in the concentration of 0.1% based on the amount of reactants.

In a further embodiment of the present invention wherein the hydroxyl values of the compounds prepared by the process is ≤1.0 mg KOH/g In an embodiment of the present invention wherein the compounds are useful as lubricant base oils and suitable for preparing lubricant formulations for application in automotive lubricants, metal working oils, hydraulic oils and other industrial oils.

Vegetable oils provide most of the desirable lubricant properties such as good boundary lubrication, high viscosity index, high flash point and low volatility. Synthetic esters prepared from renewable resources like vegetable oils exhibit better performance at a lower cost compared to mineral oil based synthetic esters. A new class of vegetable oil based polyol esters are prepared by esterification of different polyols having 5-6 carbon atoms and 2-4 hydroxyl groups with 10-undecenoic acid or/and undecanoic acid with a hydroxyl value of ≤1.0 mg KOH/g. The resulting esters were characterized for lubricant properties like viscosity, viscosity index, pour point, flash point and copper corrosion tests. The properties indicate their potential as promising lubricant base stocks for automotive lubricants, metal working oil, hydraulic oil and other industrial applications.

According to the present invention, a new range of polyol esters are obtained by esterifying polyols with 10-undecenoic acid, undecanoic acid or their mixtures. Polyols used in this invention are exemplified by trimethylolpropane, pentaerythritol, trimethylolethane and neopentyl glycol. The polyol esters were prepared by esterification with 10-undecenoic acid/undecanoic acid or their mixtures in presence of stannous chloride under nitrogen atmosphere at elevated temperature preferably in the range of 180-190° C. with excess of carboxylic acids. The excess acid was distilled preferably at temperature in the range of 140-160° C. under vacuum preferably in the range of 2-10 mm and the product was passed over basic alumina to remove acidic impurities.

All the polyol esters were characterized for hydroxyl value, total acid number and evaluated for the properties like viscosity, viscosity index, pour point, flash point and copper corrosion value and found to be potential lubricant base stocks.

Polyol esters were made by reacting carboxylic acids and polyols. Aliphatic carboxylic acids cannot be used as lubricant as they are corrosive in nature, 10-undecenoic and undecanoic acids are medium chain lower molecular weight fatty acids with higher vapour pressure and get evaporated during their use as lubricant. Melting points of 10-undecenoic acid and undecanoic acids are 23-25° C. and 28-31° C. respectively.

Total acid number (TAN) is a very important property for any lubricant. TAN indicates the amount of free acid present in the lubricant. It is known to the experts in the art of lubricant that TAN value has to be as low as possible to get a better quality lubricant. Hence use of acids as lubricant is not possible.

There are no reports on any polyol used directly as lubricant base stock.

Polyol esters prepared using medium chain fatty acids such as 10-undecenoic and undecanoic acids have man branch chains and this is an important feature for low pour point of the products.

Esters themselves are active materials with high lubricant efficacy and their raw materials, acids and polyols do not exhibit any lubricant properties.

Hence, process of esterfication creates an entirely new class of products as far as lubricant properties are concern. There is not mere enhancement of properties of known substances and starting products. These derived esters have desirable lubricant properties where as starting material are not suitable to be used as lubricants. These polyol esters not only differ significantly but entirely with regard to efficacy.

This invention is further described by the following examples which are given only for the purpose of illustration and not indented to limit the scope of the invention. Although the invention has been described in conjunction with examples and by reference to the embodiments thereof, it is evident that many alternative modifications and variations will be apparent to those skilled in the art in light of the forging description, accordingly it is intended in the invention to embrace these and all such alternatives, variations and modifications as may fall with in the spirit and scope of the appended claims.

EXAMPLE 1

Preparation of Trimethylolpropane Triesters of 10-Undecenoic Acid

Trimethylolpropane (67 g, 0.5 mole) and 10-undecenoic acid (920 g, 5.0 mole) were charged in a 4-necked reaction flask equipped with stirrer, thermometer, water condenser and a nitrogen purger. The reaction mixture was heated to 190° C. under nitrogen atmosphere in presence of stannous chloride (1.0 g). The esterification was allowed to continue until theoretical amount of water was collected. The crude product was distilled at 143° C. temperature and 3 mm vacuum to remove excess 10-undecenoic acid and passed over basic alumina to remove acidic impurities to yield the product (304 g) with acid value 0.05. The product was evaluated for viscosity, viscosity index (V.I.), pour point, flash point and copper strip corrosion and the data is provided in the following table.

| Property | Value |
|---|---|
| Viscosity at 40° C. cSt | 23.87 |
| Viscosity at 100° C. cSt: | 5.33 |
| Viscosity Index | 214 |
| Pour Point (° C.) | −36 |
| Flash point (° C.) | 286 |
| Copper strip corrosion | 1 a |
| Hydroxyl Value(mg KOH/g) | 0.3 |

The structure of the title product was established by $^{1}H$ NMR studies.

$^1H$ NMR ($CDCl_3$, δ ppm): 0.9 [t, —$CH_3$], 1.2-1.5 [m, $CH_3$—$CH_2$—, 3×(—$CH_2$—)$_5$], 1.5-1.7 [m, 3×(—CO—$CH_2$—$CH_2$)], 2.0 [q, 3×(—$CH_2$—CH═$CH_2$)], 2.3 [t, 3×(—CO—$CH_2$—)], 4.0 [s, 3×(—O—$CH_2$—)], 4.9-5.0 [m, 3×(—CH═$CH_2$)], 5.7-5.8 [m, 3×(—CH═$CH_2$)].

EXAMPLE 2

Preparation of Pentaerythritol Tetra Esters of 10-Undecenoic Acid

Pentaerythritol (68 g, 0.5 mole) and 10-undecenoic acid (920 g, 5 moles) were charged in a 4-necked reaction flask equipped with stirrer, thermometer, water condenser and a nitrogen purger. The reaction mixture was heated to 190° C. under nitrogen atmosphere in presence of stannous chloride (1.0 g). The esterification was allowed to continue until theoretical amount of water was collected. The crude product was distilled at 142° C. temperature and 2 mm vacuum to remove excess 10-undecenoic acid and passed over basic alumina to remove acidic impurities to yield the product (366.6 g) with acid value 0.17. The product was evaluated for viscosity, viscosity index (V.I.), pour point, flash point and copper strip corrosion and the data is provided in the following table.

| Property | Value |
|---|---|
| Viscosity at 40° C. cSt | 36.17 |
| Viscosity at 100° C. cSt: | 7.31 |
| Viscosity Index | 173 |
| Pour Point (° C.) | +3 |
| Flash point (° C.) | 296 |
| Copper strip corrosion | 1 a |
| Hydroxyl Value(mg KOH/g) | 0.7 |

The structure of the title product was established by $^1H$ NMR studies.

$^1H$ NMR ($CDCl_3$, δ ppm): 1.1-1.4 [m, 4×(—$CH_2$)$_5$], 1.5-1.6 [m, 4×(—CO—$CH_2$—$CH_2$)], 2.0 [q. 4×(—$CH_2$—CH═$CH_2$)], 2.3 [t, 4×(—CO—$CH_2$—)], 4.0 [s, 4×(—O—($CH_2$—)], 4.8-4.95 [m, 4×(—CH═$CH_2$)], 5.6-5.8 [m, 4×(—CH═$CH_2$)].

EXAMPLE 3

Preparation of Trimethylolethane Triesters of 10-Undecenoic Acid

Trimethylolethane (200 g, 1.66 mole) and 10-undecenoic acid (3054 g, 16.6 mole) were charged in a 4-necked reaction flask equipped with stirrer, thermometer, water condenser and a nitrogen purger. The reaction mixture was heated to 190° C. under nitrogen atmosphere in presence of stannous chloride (3.2 g). The esterification was allowed to continue until theoretical amount of water was collected. The crude product was distilled at 144° C. temperature and 3 mm vacuum to remove excess 10-undecenoic acid and passed over basic alumina to remove acidic impurities to yield the product (994.0 g) with acid value 0.11. The product was evaluated for viscosity, viscosity index (V.I.), pour point, flash point and copper strip corrosion and the data is provided in the following table.

| Property | Value |
|---|---|
| Viscosity at 40° C. cSt | 24.49 |
| Viscosity at 100° C. cSt: | 5.51 |
| Viscosity Index | 173 |
| Pour Point (° C.) | −15 |
| Flash point (° C.) | 296 |
| Copper strip corrosion | 1 a |
| Hydroxyl Value(mg KOH/g) | 0.4 |

The structure of the title product was established by $^1H$ NMR studies.

$^1H$ NMR ($CDCl_3$, δ ppm): 1.0 [s, —$CH_3$], 1.2-1.4 [m, 3×(—$CH_2$)$_5$], 1.5-1.7 [m, 3×(—CO—$CH_2$—$CH_2$)], 2.0 [q, 3×(—$CH_2$—CH═$CH_2$)], 2.3 [t, 3×(—CO—$CH_2$—)], 4.0 [s, 3×(—O—$CH_2$—)], 4.9-5.0 [m, 3×(—CH═$CH_2$)], 5.7-5.8. [m, 3×(—CH═$CH_2$)].

EXAMPLE 4

Preparation of Neopentylglycol Diesters of 10-Undecenoic Acid

Neopentylglycol (260 g, 2.5 mole) and 10-undecenoic acid (2760 g, 15.0 mole) were charged in a 4-necked reaction flask equipped with stirrer, thermometer, water condenser and a nitrogen purger. The reaction mixture was heated to 190° C. under nitrogen atmosphere in presence of stannous chloride (3.0. g). The esterification was allowed to continue until theoretical amount of water was collected. The yielded crude product was distilled at 143° C. temperature and 3 mm vacuum to remove excess 10-undecenoic acid and passed over basic alumina to remove acidic impurities to yield the product (1042.0 g) with acid value 0.05. The product was evaluated for viscosity, viscosity index (V.I.), pour point, flash point and copper strip corrosion and the data is provided in the following table.

| Property | Value |
|---|---|
| Viscosity at 40° C. cSt | 11.21 |
| Viscosity at 100° C. cSt: | 3.20 |
| Viscosity Index | 164 |
| Pour Point (° C.) | −33 |
| Flash point (° C.) | 254 |
| Copper strip corrosion | 1 a |
| Hydroxyl Value(mg KOH/g) | 0.3 |

The structure of the title product was established by $^1H$ NMR studies.

$^1H$ NMR ($CDCl_3$, δ ppm): 0.87 [s, (—$CH_3$)$_2$], 1.2-1.4 [m, 2×(—$CH_2$)$_5$], 1.6 [m, 2×(—CO—$CH_2$—$CH_2$)], 2.0 [q, 2×(—$CH_2$—CH═$CH_2$)], 2.3 [t, 2×(—CO—$CH_2$—)], 3.8 [s, 2×(—O—$CH_2$—)], 4.9-5.0 [m, 2×(—CH═$CH_2$)], 5.6-5.8 [m, 2×(—CH═$CH_2$)].

EXAMPLE 5

Preparation of Trimethylolpropane Triesters of Undecanoic Acid

Trimethylolpropane ((93.8 g, 0.7 mole) and undecanoic acid (1302 g, 7.0 mole) were charged in a 4-necked reaction flask equipped with stirrer, thermometer, water condenser and a nitrogen purger. The reaction mixture was heated to 190° C. under nitrogen atmosphere in presence of stannous chloride (1.4 g). The esterification was allowed to continue until theoretical amount of water was collected. The yielded crude product was distilled at 155° C. temperature and 7 mm vacuum to remove excess undecanoic acid and passed over basic alumina to remove acidic impurities to yield the product (430.0 g) with acid value 0.57. The product was evaluated for viscosity, viscosity index (V.I.), pour point, flash point and copper strip corrosion and the data is provided in the following table.

| Property | Value |
| --- | --- |
| Viscosity at 40° C. cSt | 29.50 |
| Viscosity at 100° C. cSt: | 6.03 |
| Viscosity Index | 157 |
| Pour Point (° C.) | −9 |
| Flash point (° C.) | 296 |
| Copper strip corrosion | 1 a |
| Hydroxyl Value(mg KOH/g) | 0.8 |

The structure of the title product was established by $^1$H NMR studies.

$^1$H NMR ($CDCl_3$, δ ppm): 0.8-0.9 [m, 4×—($CH_3$)], 1.15-1.35 [bs, 3×(—$CH_2$)$_7$], 1.35-1.55 [m, CH3-CH2-C] 2.3 [t, 3×(—CO—$CH_2$—)], 4.0 [s, 3×(—O—$CH_2$—)],

EXAMPLE-6

Preparation of Trimethylolpropane Triesters of 10-Undecenoic Acid and Undecanoic Acid Mixture in 1:1 Molar Ratio Trimethylolpropane was charged (93.8 g, 0.7 mole) with 10-undecenoic acid and undecanoic acid mixture in 1:1 molar ratio (1288 g, 7.0 mole) in a 4-necked reaction flask equipped with stirrer, thermometer, water condenser and a nitrogen purger. The reaction mixture was heated to 190° C. under nitrogen atmosphere in presence of stannous chloride (1.4 g). The esterification was allowed to continue until theoretical amount of water was collected. The yielded crude product was distilled at 156° C. temperature and 8 mm vacuum to remove excess 10-undecenoic and undecanoic acids and passed over basic alumina to remove acidic impurities to yield the product (427.5 g) with acid value 0.11. The product was evaluated for viscosity, viscosity index (V.I.), pour point, flash point and copper strip corrosion and the data is provided in the following table.

| Property | Value |
| --- | --- |
| Viscosity at 40° C. cSt | 33.56 |
| Viscosity at 100° C. cSt: | 6.77 |
| Viscosity Index | 165 |
| Pour Point (° C.) | −18 |
| Flash point (° C.) | 292 |
| Copper strip corrosion | 1 a |
| Hydroxyl Value(mg KOH/g) | 0.6 |

EXAMPLE 7

Preparation of Trimethylolpropane Triesters of 10-Undecenoic Acid and Undecanoic Acid Mixture in 3:1 Molar Ratio Trimethylolpropane (33.5 g, 0.25 mole) was charged with 10-undecenoic acid and undecanoic acid mixture in 3:1 molar ratio (461.3 g, 2.5 mole) in a 4-necked reaction flask equipped with stirrer, thermometer, water condenser and a nitrogen purger. The reaction mixture was heated to 190° C. under nitrogen atmosphere in presence of stannous chloride (0.49 g). The esterification was continued until theoretical amount of water was collected. The yielded triester was distilled at 158° C. temperature and 8 mm vacuum to remove excess 10-undecenoic and undecanoic acids and passed over basic alumina to remove acidic impurities to yield the product (140.0 g) with acid value 0.05. The product was evaluated for viscosity, viscosity index (V.I.), pour point, flash point and copper strip corrosion and the data is provided in the following table.

| Property | Value |
| --- | --- |
| Viscosity at 40° C. cSt | 27.98 |
| Viscosity at 100° C. cSt: | 5.96 |
| Viscosity Index | 150 |
| Pour Point (° C.) | −24 |
| Flash point (° C.) | 302 |
| Copper strip corrosion | 1 a |
| Hydroxyl Value(mg KOH/g) | 0.3 |

ADVANTAGES OF THE INVENTION

1. Polyol esters of 10-Undecenoic acid have superior lubricant properties like low pour points, high viscosity index and high flash points. Vegetable oils with high oleic content are considered to be potential candidates to prepare bio-lubricant base stocks because of their good low temperature properties and oxidation stability. This high oleic content is generally achieved by genetic modification of vegetable oils like soybean, rape seed or sun flower or by chemical modifications like selective hydrogenation of polyunsaturated oils like soybean oil. 10-undecenoic acid is a monounsaturated fatty acid like oleic acid and polyol esters of 10-Undecenoic acid also have low temperature properties and they also may exhibit good thermal and oxidative properties like polyol esters of high oleic vegetable oils.
2. Although polyol esters prepared with undecanoic acid have relatively high pour points, they will have superior oxidation and thermal stability properties because of their high saturation content and they can be used in application where very low temperature requirement is not a criteria.

We claim:

1. A lubricant base stock oil comprising:

polyol esters of a medium chain fatty acid, said esters having hydroxyl values of ≤1.0 mg KOH/g, wherein said medium chain fatty acid is 10-undecenoic acid;

said polyol is selected from the group consisting of trimethylolpropane, trimethylolethane, neopentylglycol and pentaerythritol;

and said lubricant base stock oil is suitable for preparing a lubricating formulation for applications in automotive lubricants, metal working oils, hydraulic and other industrial oils.

2. The esters as claimed in claim 1 for lubricant base stock applications selected from the group consisting of:

Trimethylolpropane Triesters of 10-Undecenoic acid,
Pentaerythritol Tetraesters of 10-Undecenoic acid,
Trimethylolethane Triesters of 10-Undecenoic acid, Neopentylglycol Diesters of 10-Undecenoic acid, and Trimethylolpropane Triesters of 10-Undecenoic Acid and Undecanoic acid blends.

3. A process for preparation of polyol esters compounds comprising the steps of:

reacting a medium chain fatty acid selected from the group consisting of 10-undecenoic acid, undecanoic acid and their mixtures, with terminal alkenyl group or its hydrogenated form or their mixtures with di, tri and tetrahydric polyols in presence of a catalyst under inert atmosphere at a temperature ranging between 180 to 190° C. for a period ranging between 5 to 7 hours to obtain a polyol ester compound and, purifying the compound by distilling out unreacted acid at reduced pressure and treatment with basic alumina, wherein hydroxyl value of the compound prepared by the process is ≤1.0 mg KOH/q.

4. A process as claimed in claim 3 wherein the di, tri and tetrahydric polyols are selected from the group consisting of neopentylglycol, trimethylolpropane, trimethylolethane and pentaerythritol.

5. A process as claimed in claim 3 wherein the reaction is carried out using a molar ratio of polyol to carboxylic acid or their mixtures in the range of 1:6 to 1:10.

6. A process as claimed in claim 3 wherein a stannous chloride is used as catalyst in the concentration of 0.1% based on the amount of polyol and fatty acid.

7. A process as claimed in claim 3 wherein the compounds are useful as lubricant base oils and suitable for preparing lubricant formulations for application in automotive lubricants, metal working oils, hydraulic oils and other industrial oils.

8. A compound selected from the group consisting of 2,2-di[(10-undecenoyloxy)methyl]butyl 10-undecenoate, 3-(10-undecenoyloxy)-2,2-di[(10-undecenoyloxy)methyl]propyl 10-undecenoate, 2-methyl-3(10-undecenoyloxy)-2-[(10-undecenoyloxy)methyl]propyl 10-undecenoate and 2,2-dimethyl-3-(10-undecenoyloxy)propyl 10-undecenoate.

* * * * *